US011806474B2

(12) United States Patent
Blandin et al.

(10) Patent No.: US 11,806,474 B2
(45) Date of Patent: Nov. 7, 2023

(54) DEVICE FOR SUPPLYING THERAPEUTIC GAS, PARTICULARLY NO OR $N_2O$, TO A PATIENT

(71) Applicant: L'AIR LIQUIDE SOCIETE ANONYME POUR L'ETUDE ET L'EXPLOITATION DES PROCEDES GEORGES CLAUDE, Paris (FR)

(72) Inventors: Yann Blandin, Gentilly (FR); Louise Thevenet, Gentilly (FR); Marie Amory, Sainte Luce sur Loire (FR)

(73) Assignee: L'AIR LIQUIDE, SOCIETE ANONYME POUR L'ETUDE AND L'EXPLOITATION DES PROCEDES GEORGES CLAUDE, Paris (FR)

( * ) Notice: Subject to any disclaimer, the term of this patent is extended or adjusted under 35 U.S.C. 154(b) by 417 days.

(21) Appl. No.: 17/094,294

(22) Filed: Nov. 10, 2020

(65) Prior Publication Data
US 2021/0146086 A1 May 20, 2021

(30) Foreign Application Priority Data

Nov. 15, 2019 (FR) ...................................... 1912769

(51) Int. Cl.
*A61M 16/00* (2006.01)
*A61M 16/20* (2006.01)
*A61M 16/12* (2006.01)

(52) U.S. Cl.
CPC .......... *A61M 16/024* (2017.08); *A61M 16/12* (2013.01); *A61M 16/201* (2014.02);
(Continued)

(58) Field of Classification Search
CPC ............ A61M 2205/52; A61M 16/024; A61M 2205/84; A61M 16/12; A61M 2202/0208;
(Continued)

(56) References Cited

U.S. PATENT DOCUMENTS

| 2003/0116159 A1 | 6/2003 | Orr et al. |
| 2003/0168062 A1* | 9/2003 | Blythe .............. A61M 15/0086 128/203.29 |

(Continued)

FOREIGN PATENT DOCUMENTS

| EP | 0 560 928 | 9/1993 |
| EP | 1 516 639 | 3/2005 |

(Continued)

*Primary Examiner* — Joseph D. Boecker
(74) *Attorney, Agent, or Firm* — Quantum Patent Law Firm; Seongyoune Kang

(57) ABSTRACT

Disclosed is a device for supplying therapeutic gas, notably $NO/N_2$ or $O_2/N_2O$ mixtures, including an internal passage with a valve for conveying and controlling the flow of therapeutic gas in the internal passage, a control unit controlling the valve, a graphic display for displaying choices that can be selected by a user, and a selector, such as touch-sensitive keys displayed on the graphic display for making a selection from among the selectable choices displayed on the graphic display. The control unit is configured to count a total number of patients treated by administration of the therapeutic gas from the selection, by a user, via the selector, of a first given choice corresponding to the start of a treatment by administering the therapeutic gas to a patient concerned.

20 Claims, 2 Drawing Sheets

Figure 1:
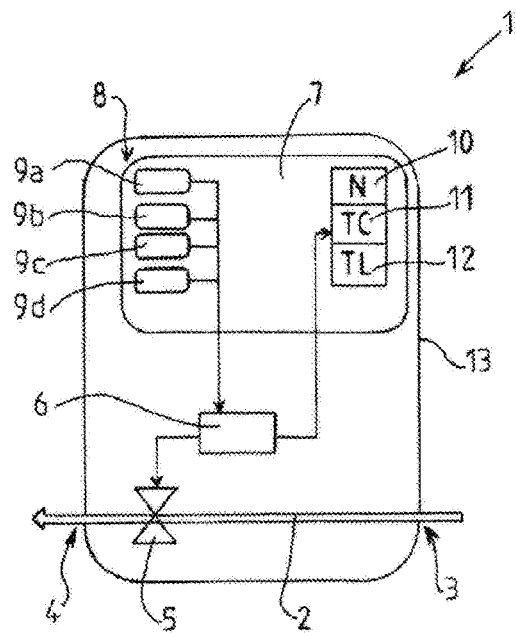

(52) U.S. Cl.
CPC ............... *A61M 2202/0208* (2013.01); *A61M 2202/0275* (2013.01); *A61M 2202/0283* (2013.01); *A61M 2205/505* (2013.01); *A61M 2205/52* (2013.01); *A61M 2205/583* (2013.01)

(58) Field of Classification Search
CPC .. A61M 2202/0275; A61M 2202/0283; A61M 2205/505; A61M 2205/583; A61M 2205/502; A61M 2205/3553–3561; A61M 16/201; A61M 16/1005; A61M 16/0891; A61M 16/1065; A61M 16/16; A61M 16/22; A61M 2016/0039; A61M 2016/1035; A61M 16/204; A61M 2205/3334; A61M 2205/8206; A61M 16/00; A61M 16/0057; A61M 16/0066; A61M 16/022; A61M 15/008; F17C 2250/032; F17C 2250/0473; G16H 50/70; G16H 10/60; G16H 15/00; G16H 20/00; G16H 20/10; G16H 20/40; G16H 40/20; G16H 40/60; G16H 40/63; G16H 40/67; G16H 50/20; H04Q 2209/70; H04Q 9/00; A61B 5/0002; A61B 5/0004; A61B 5/0015; A61B 5/002; A61B 5/0022; A61B 5/0024; A61B 5/02; A61B 5/085; A61B 5/7435; A61B 5/7465

See application file for complete search history.

(56) References Cited

U.S. PATENT DOCUMENTS

| | | | |
|---|---|---|---|
| 2006/0207594 | A1* | 9/2006 | Stenzler .............. A61M 16/204 128/204.22 |
| 2012/0240927 | A1* | 9/2012 | Bathe .................. A61M 16/085 128/203.12 |
| 2014/0130905 | A1* | 5/2014 | Schon ................... A61M 16/01 137/486 |
| 2015/0273175 | A1 | 10/2015 | Acker et al. |
| 2015/0320951 | A1 | 11/2015 | Acker et al. |
| 2015/0320953 | A1* | 11/2015 | Acker ............... A61M 16/1005 128/203.14 |
| 2017/0348503 | A1* | 12/2017 | Westermark ...... A61M 16/0078 |
| 2017/0368280 | A1* | 12/2017 | Dermel ................ G09B 23/288 |
| 2018/0243527 | A1* | 8/2018 | Zapol .................. A61M 16/107 |
| 2018/0243528 | A1* | 8/2018 | Zapol ..................... A61K 33/00 |

FOREIGN PATENT DOCUMENTS

| | | | |
|---|---|---|---|
| JP | H11-192303 | 7/1999 | |
| WO | 92/10228 | 6/1992 | |
| WO | 02/40914 | 5/2002 | |
| WO | WO-2007106804 A2 * | 9/2007 | ............ A61B 34/25 |
| WO | 2012/094008 | 7/2012 | |
| WO | WO-2015037002 A2 * | 3/2015 | ........ A61M 16/0057 |
| WO | WO-2016159889 A1 * | 10/2016 | ............ A61M 16/00 |

* cited by examiner

DEVICE FOR SUPPLYING THERAPEUTIC GAS, PARTICULARLY NO OR N₂O, TO A PATIENT

The present invention relates to a device for supplying therapeutic gas, particularly nitric oxide (NO) or nitrous oxide ($N_2O$), and also to an installation for administering gas to a patient comprising such a therapeutic-gas supply device.

Inhaled nitric oxide, or NOi, is a gaseous medicament commonly used to treat patients suffering from acute pulmonary arterial hypertension, particularly pulmonary vasoconstrictions in adults or children, including the newborn (PPHN), as described for example in EP-A-560928 or EP-A-1516639.

An installation for applying NOi treatment, commonly referred to as an NO-administration installation, conventionally comprises one or more cylinders of $NO/N_2$ mixture supplying an NO-treatment administration and/or monitoring device, a medical ventilator for delivering a respiratory gas, such as an $O_2/N_2$ mixture or air, to which the NO (i.e. $NO/N_2$) is added, and a patient kit notably comprising a respiratory interface, such as a tracheal tube, and one or more flexible pipes.

Such an NO-administration installation is used in a hospital environment to administer the NOi treatment and thus care for hospitalized patients who need to inhale NO in order to treat their pulmonary arterial hypertension.

Examples of such NO-administration installations are given in documents WO-A-2012/094008, US-A-2015/320951, US-A-2015/273175, JP-A-H11192303, WO-A-02/40914 and US-A-2003/116159.

Now, the duration of patient treatment varies from one patient to another, namely from a few hours up to several days. As a result, within hospitals, it is very difficult to trace and record the number of patients who have been treated with NOi over a given period, for example of one or more months, or even an entire year, this being very different from the case with the other medicaments, even though this information regarding the number of patients treated is of utmost relevance to the hospitals which are obliged to guarantee correct use of the medicament and to correlate the number of prescriptions against their hospital activity.

A similar range of problems also exists with other therapeutic gases, particularly equimolar mixtures of oxygen and nitrous oxide (MEOPA), i.e. $O_2/N_2O$ mixtures, or even other medical gases.

In an attempt to address this problem, certain administration devices or gas cylinders count the number of hours of use of the therapeutic gas in order from this, and on the basis of a fixed mean duration of use, to deduce an approximate number of patients treated.

Now, it will be appreciated that this approach is not ideal because it is based on a single mean duration, whereas the durations of use vary greatly from one patient to another. Thus it will be readily appreciated that the quantities of gas used in adults are very different from those used in newborns. The resulting calculation is therefore extremely inaccurate, or even completely erroneous.

In addition, this approach also leads to errors because it relies on calculations done by the user, who may make a mistake in performing these calculations.

Finally, if a gas cylinder is inadvertently left open, the gas delivered will be considered as having been used to care for patients, even though it has been lost, and this once again will falsify the calculation.

The problem therefore is that of being able to accurately and reliably count the number of patients treated by inhaling therapeutic gas, notably NO, which can be consulted at any moment by the user, such as the care-giving staff, and which is automated in such a way as to supply information that is useful to the user, and do so instantaneously, without the user having to perform the smallest of calculations for himself, particularly in the context of the supply of $NO/N_2$ mixtures to a patient having need of such treatment, notably for treating their pulmonary arterial hypertension or hypo-oxygenation of their blood.

A solution according to the invention therefore relates to a device for supplying therapeutic gas, comprising:
- an internal passage for conveying a flow of therapeutic gas between (at least) a gas inlet and (at least) a gas outlet,
- valve means for controlling the flow of therapeutic gas in the internal passage,
- control means configured to control at least the valve means,
- a graphic display configured to display (at least) choices that can be selected by a user, and possibly other information, and
- selection means configured to make a selection from among the selectable choices displayed on the graphic display.

According to the invention, the control means are configured to count a total number (N) of patients treated by administration of the therapeutic gas from the selection, by a user, via the selection means, of a first given choice corresponding to the start of a treatment by administering the therapeutic gas to a patient concerned.

According to the embodiment considered, the therapeutic-gas supply device of the invention may comprise one or more of the following features:
- the control means cooperate with the graphic display to display the counted total number (N) of patients treated.
- the control means comprise at least one microprocessor, preferably at least one microcontroller.
- said at least one microprocessor is arranged on an electronic board.
- the control means comprise at least one microprocessor using one or more algorithms.
- the selection means comprise one or more selection keys.
- the graphic display comprises a display screen, typically a digital screen, preferably a touchscreen.
- the selection key or keys are one or more virtual keys displayed on the touchscreen, namely one or more touch-sensitive keys.
- the graphic display is configured to display the virtual selection key(s) in the form of one or more selection windows.
- the graphic display comprises a display screen in colour or in black and white, or both.
- the control means are configured to count a total number (N) of patients treated by incrementing a patients counter, particularly an internal counter of the microprocessor.
- the control means are configured to increment the total number (N) of patients treated by +1 in response to a selection, by the user, of the first given choice corresponding to the start of a treatment by administering therapeutic gas to a patient concerned.
- the control means are configured to operate the valve means and begin a supply of therapeutic gas in response to a selection, by the user, of the first given choice corresponding to the start of a treatment by administering therapeutic gas to a patient concerned.

alternatively, the control means are configured to operate the valve means and begin a supply of therapeutic gas in response to a selection, by the user, of the first given choice corresponding to the start of a treatment by administering therapeutic gas to a patient concerned, followed by a validation (i.e. confirmation) of said selection of the first given choice, said validation preferably being performed by the user selecting a Validate key, particularly a virtual Validate key displayed on the graphic display.

the control means are also configured to determine a total duration of treatment for each patient treated which corresponds to the period of time elapsed between the user selecting:
   the first given choice corresponding to the start of a treatment by administering the therapeutic gas to a patient concerned, and
   a second given choice corresponding to the end of the treatment by administering the therapeutic gas to said patient concerned.

the control means are further configured to:
   temporarily interrupt the determining of the total duration of treatment for a patient concerned after:
      either the user selects the second given choice corresponding to the end of the treatment,
      or the user selects a third given choice corresponding to a suspension of treatment with temporary interruption of the administration of therapeutic gas to said patient concerned, and
   resume determining the total duration of treatment for said patient concerned after:
      either the user reselects the first given choice corresponding to the start of a treatment by administering the therapeutic gas, that is to say makes an additional selection of the first given choice for the same patient,
      or the user selects a fourth given choice corresponding to resumption of a treatment by administering the therapeutic gas to said given patient.

the control means are also configured not to increment the patients counter after the user reselects the first given choice corresponding to the start of a treatment or selects the fourth given choice corresponding to the resumption of treatment for a given patient. This is because a reselection of the first given choice or a selection of the fourth given choice is interpreted/considered by the control means, particularly the microprocessor, to indicate the resumption of the one same treatment of the one same patient, following a temporary pause in this treatment in this patient.

the selection keys comprise:
   a "Start treatment" key commanding the start of supply of therapeutic gas, and
   an "End treatment" key commanding the stopping of the supply of therapeutic gas.

the "Start treatment" key and the "End treatment" key are the one same key commanding the start and end of the supply of gas.

the "Start treatment" key and the "End treatment" key are different keys.

the selection keys also potentially comprise:
   a "Pause treatment" key commanding a pause in the supply of therapeutic gas, and/or
   a "Resume treatment" key commanding a resumption (following a pause) of the supply of therapeutic gas.

the "Pause treatment" key and the "Resume treatment" key are the one same key commanding the pausing and resumption of the supply of gas.

the "Pause treatment" key and the "Resume treatment" key are different keys.

according to another embodiment, the "Pause treatment" key and the "End treatment" key are the one same key commanding a definitive or temporary stopping (i.e. pausing) of the supply of gas.

according to yet another embodiment, the "Start treatment" key and the "Resume treatment" key are the one same key commanding a start (i.e. initial or resumption after a pause) of the supply of gas.

the control means are also configured to determine, from the total number (N) of patients treated, which has been counted up, and from the total treatment durations determined for the treated patients:
   the number of short treatments (TC) for which the total treatment duration is below a preset threshold duration. In other words, the number TC corresponds to the number of patients who have undergone a treatment that has quickly been interrupted, typically after less than 3 hours, because this treatment was not effective, was having negative side-effects or for some other reason, and/or
   the number of long treatments (TL) for which the total treatment duration is above said preset threshold duration. In other words, the number TL corresponds to the number of patients who have undergone a treatment of long duration because it has been effective in these patients, for example over a duration that may be as long as several days.

according to one particular embodiment, the control means are also configured not to increment the total number (N) of patients treated by +1 (i.e. not to count them) when the total treatment duration determined is below a preset minimum duration which is below the preset threshold duration, for example a preset minimum duration less than or equal to 1 hour, preferably less than or equal to 30 minutes. This is because use of the device for a short minimum duration generally corresponds to an exceptional situation that does not correspond to the treatment of a patient, for example to correcting a setup error, performing a demonstration for training purposes or the like, which exceptional situation, in order not to falsify the calculation of the total number (N) of patients treated, must not be counted.

the number of long treatments (TL) is equal to the total number (N) of patients treated minus the number of short treatments (TC), namely: TL=N−TC. Or, expressed differently, N=TC+TL or TC=N−TL.

the control means cooperate with the graphic display to also display the number of short treatments (TC) and/or the number of long treatments (TL).

it further comprises memory storage means configured to store:
   the total number (N) of patients treated,
   the number of short treatments (TC),
   the number of long treatments (TL),
   the choices selectable by the user, and/or
   the preset threshold duration,
   and/or possibly the preset minimum duration.

the threshold duration is less than or equal to 5 hours, typically of the order of 3 h to 4 h, for example 3h, when the therapeutic gas is NO.

the minimum duration is less than or equal to 1 h, for example of the order of 30 minutes.

the threshold duration is adjustable and/or the minimum duration is adjustable.

the memory storage means comprise one or more memories for recording and storing data, for example one or more volatile or non-volatile memories, for example of the flash memory or some other type.

at least one memory (e.g. flash) is sited on a or the electronic board.

it further comprises electrical-current supply means which supply electrical current to such components of the device as require current in order to operate, such as the display, the microprocessor, the memory . . . . The electrical-current supply means may, in the conventional way, comprise one (or more) rechargeable or non-rechargeable battery(ies), a power cord and an electric plug that can be connected to the mains network (110/220 V), a current transformer, etc.

it further comprises a rigid external casing or housing in which all or some of the components of the device are arranged, particularly the control means, the internal passage, the valve means, etc.

the graphic display is arranged in a wall of the rigid external casing.

the control means are configured to control (at least) the valve means so as to adjust the flow rate of therapeutic gas circulating in the internal passage.

the valve means comprise at least one proportional (electro)valve or several electrovalves, preferably several electrovalves arranged in parallel.

it further comprises a flowmeter device arranged on the gas passage so as to determine (i.e. measure) the flow rate of therapeutic gas circulating in the internal passage.

the flowmeter device is of the hot-wire or differential-pressure type.

the flowmeter device cooperates with the control means.

it comprises re-zeroing (RESET) means allowing the counter or counters to be reset, for example a RESET key or the like.

The invention also relates to an installation for administering gas to a patient, comprising:
  at least one source of therapeutic gas,
  a therapeutic-gas supply device according to the invention, supplied with therapeutic gas by said at least one source of therapeutic gas, and
  a gas supply line supplied with therapeutic gas by the therapeutic-gas supply device.

According to the embodiment considered, the gas administering installation of the invention may comprise one or more of the following features:
  it further comprises a medical ventilator, that is to say a ventilation assistance apparatus, in fluidic communication with the gas supply line.
  the medical ventilator is fluidically connected to the supply line to supply said supply line with air or with an $N_2/O_2$ mixture.
  the source(s) of therapeutic gas contain/s NO, particularly an $NO/N_2$ mixture.
  the source of therapeutic gas contains an $NO/N_2$ mixture containing less than 2000 ppm by volume of NO, the rest being nitrogen, preferably less than 1000 ppm by volume of NO, the rest being nitrogen.
  as a preference, the source of therapeutic gas contains an $NO/N_2$ mixture containing from 250 to 900 ppm by volume of NO, the rest being nitrogen, for example of the order of 800 ppm by volume of NO, the rest being nitrogen.
  alternatively, at least one source of therapeutic gas contains an $O_2/N_2O$ mixture, preferably an equimolar (50/50 mol %) mixture of oxygen and of nitrous oxide, i.e. contains MEOPA.
  alternatively, the source of therapeutic gas contains oxygen, and in particular comprises an oxygen container or an oxygen line.
  alternatively, the source of therapeutic gas contains argon or an argon/oxygen mixture.
  it further comprises a gas humidifier arranged on the gas supply line, preferably downstream of the point at which the therapeutic-gas supply device is fluidically connected to said gas supply line so as to supply it with therapeutic gas.
  it further comprises a line for recovering the gases exhaled by the patient.
  the gas supply line and the exhaled-gas recovery line are connected to a connection piece, preferably a Y-piece, and define a patient circuit.
  the gas supply line forms an inspiratory branch of the patient circuit.
  the exhaled-gas recovery line forms an expiratory branch of the patient circuit.
  the gas supply line is fluidically connected to an outlet port of the medical ventilator so as to collect and convey the gas delivered by the medical ventilator.
  the exhaled-gas recovery line is fluidically connected to an inlet port of the medical ventilator so as to supply the medical ventilator with all or some of the gases exhaled by the patient and thus determine whether there is one or more potential gas leaks.
  the exhaled-gas recovery line potentially (i.e. this is not compulsory) comprises a $CO_2$ removal device allowing the elimination of the $CO_2$ present in the gases exhaled by the patient.
  the exhaled-gas recovery line potentially (i.e. this is not compulsory) comprises a filter.
  at least one source of therapeutic gas comprises one or more gas container(s), particularly one or more pressurized-gas cylinder(s).
  the gas container(s) is/are equipped with a gas distribution valve.
  the gas distribution valve is a valve with or without inbuilt regulator.
  the gas distribution valve is made of copper alloy, such as brass.
  the gas container(s) is/are equipped with a protective bonnet arranged around the gas distribution valve.
  the bonnet is made of a polymer (i.e. plastic) material, of metal, or of combinations of these.
  the fluid container(s) is/are a pressurized-gas cylinder containing, when full, a gas mixture, particularly $NO/N_2$, at a pressure of at least 150 to 200 bar abs, or even at least 250 to 300 bar abs.
  the fluid container has a cylindrical, particularly ogival, overall shape.

According to another aspect, the invention also relates to a therapeutic treatment method involving administering to a patient a therapeutic gas, particularly NO, such as an NO/nitrogen mixture, wherein a gas administering installation and/or a therapeutic-gas supply device according to the invention is/are used to supply to said patient said therapeutic gas, particularly NO, such as an NO/nitrogen mixture, to a patient suffering from pulmonary hypertension, whether this be an adult, an adolescent, a child or a newborn, for example a newborn suffering from persistent pulmonary hypertension of the newborn (PPHN).

Depending on the embodiment considered, the NO/nitrogen mixture may be diluted with air or with a nitrogen/oxygen mixture before being supplied to the patient. As a preference, the air or the nitrogen/oxygen mixture is supplied by a medical ventilator.

Figure 2:
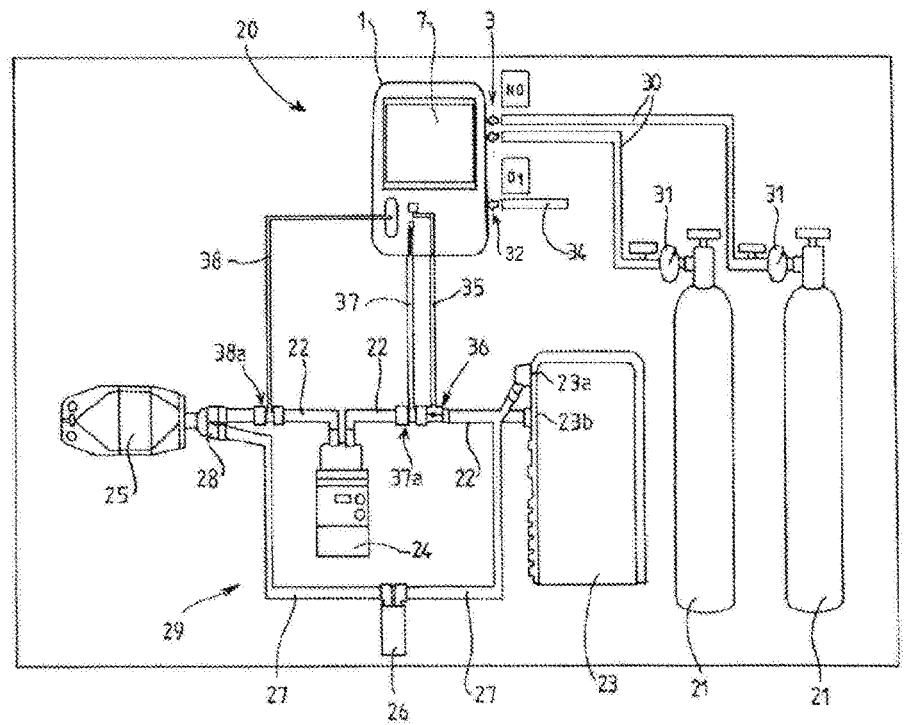
Figure 3:
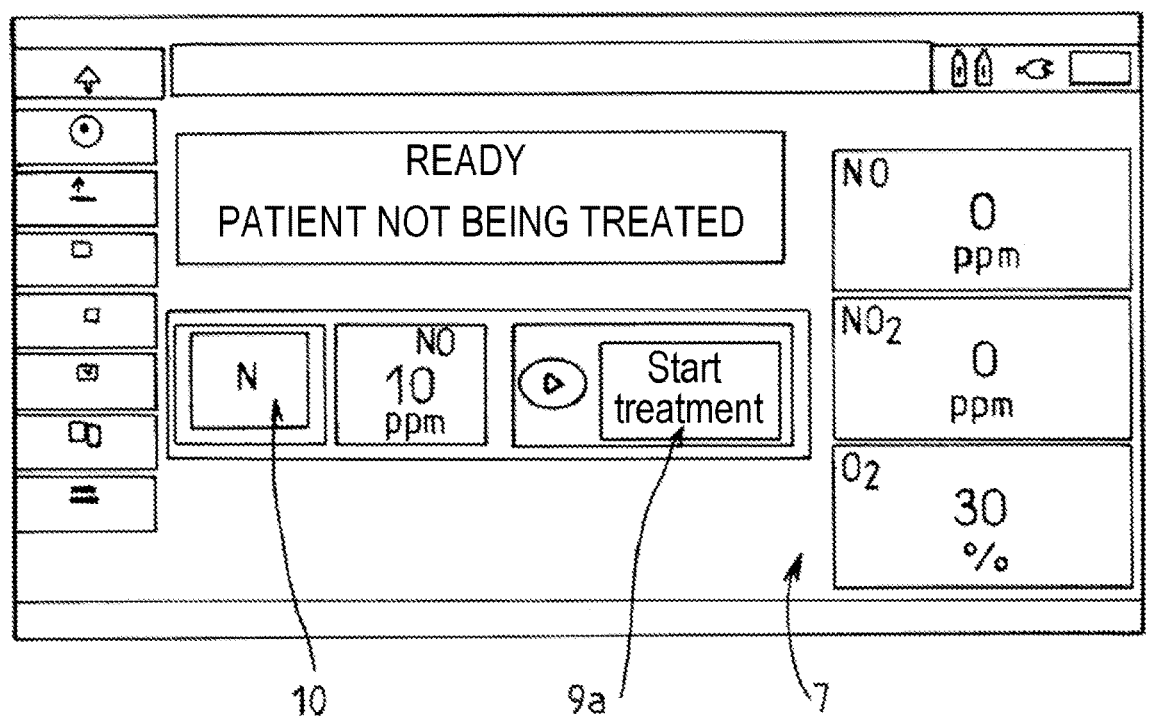

The invention will now be better understood by virtue of the following detailed description, which is given by way of non-limiting illustration, and with reference to the appended figures, in which:

FIG. 1 schematically indicates one embodiment of a therapeutic-gas supply device according to the invention, FIG. 2 schematically indicates one embodiment of a gas administering installation according to the invention, and FIG. 3 schematically indicates one embodiment of a screen of the gas supply device according to the invention.

FIG. 1 schematically indicates one embodiment of a therapeutic-gas supply device 1 according to the invention, comprising a rigid housing 13, for example made of polymer, in which there is arranged an internal passage, such as a duct, for conveying a flow of therapeutic gas.

In this embodiment, we consider, by way of example of a therapeutic gas, a flow of gas based on NO, namely a mixture of nitric oxide and of nitrogen, or $NO/N_2$.

The flow of NO-based gas enters and circulates in the internal passage between a (or more than one) gas inlet 3 and a gas outlet 4. The gas inlet 3 and outlet 4 may for example be borne by connectors or mechanical-connection and fluidic-connection end fittings borne by the housing 13 of the device 1, to which gas lines used for conveying the gas, for example flexible tubes or the like, can be attached, as explained hereinafter.

Valve means 5, i.e. a (or more than one) valve device(s), for example a plurality of electrovalves arranged in parallel, are arranged on the internal passage and allow control of the flow of therapeutic gas that circulates in the internal passage 2 in the direction extending from the gas inlet 3 to the gas outlet 4. Of course, use may also be made of other valve means, for example a (or more than one) proportional (electro)valve(s).

The valve means 5 are operated by control means 6, i.e. a (or more than one) control device(s), arranged in the housing 13, typically an electronic board comprising a (or more than one) microprocessor(s), typically a (or more than one) microcontroller(s), running one or more algorithm(s). The control means 6 notably make it possible to adjust or control the flow rate of gas passing through the valve means 5.

In this way, the control means 6 can control the valve means 5, such as electrovalves arranged in parallel, and namely can open or close all or some of these valves in order to obtain a gas flow rate (Q) determined/calculated by the microcontroller on the basis of a value that is regulated/set for example by the user, and as a function of the flow rate (Q') of gas, i.e. air, delivered by the ventilator 23, as explained hereinafter.

A (or more than one) flowmeter (not depicted) is also provided, this being arranged on the internal passage, upstream and/or downstream of the valve means 5 so as to determine the flow rate (Q) of NO-based gas. The flowmeter may be of the differential-pressure, hot-wire or some other type. It cooperates with the control means 6 in order to supply them with measurements.

Moreover, the housing 13 comprises a graphic display 7, preferably a touchscreen, used to display various items of information or data, particularly various choices 9a-9d that a user can select. These choices may be displayed in windows or the like displayed on the touch/digital screen of the graphic display 7.

The graphic display 7 is also configured to show one or more curves, graphs, alarms, icons, etc. or any other item of information or data of use to the user, such as the care-giving staff.

Also provided are selection means 8, i.e. a (or more than one) selection device, allowing the user to make a selection among the selectable choices 9a-9d which are displayed on the graphic display 7, namely to choose between several options proposed and displayed on the screen, or to confirm/validate or reject a choice (i.e. an option), or else to make adjustments or settings, for example to select the desired value for the flow rate.

The selection means 8 typically comprise selection keys or buttons that the user can actuate. Advantageously, the selection means 8 are virtual keys operated by touch, namely touch-sensitive keys, displayed on the graphic display 7 which is itself a touchscreen.

According to the present invention, the control means 6 are also configured to count a total number (N) of patients treated by administration of the therapeutic gas from the selection, by a user, via the selection means 8, particularly a touch-sensitive key displayed on the graphic display 7, of a first given choice 9a corresponding to the start of a treatment by administering the therapeutic gas to a patient concerned. For example, the start of a treatment may be initiated by the user pressing with a digit on a "Start treatment" key that commands the start of the supply of therapeutic gas.

The total number (N) of patients treated is counted by incrementing a counter, for example a counter of the microprocessor or the like, in increments of +1.

Stated differently, as soon as a treatment by administering therapeutic gas, such as NO, to a patient is to begin, the user presses on the "Start treatment" touch-sensitive key displayed on the graphic display 7, which corresponds to the initiation, i.e. the starting, of this treatment, and this increments by +1 the counter which keeps count of the total number (N) of patients treated.

The total number (N) of patients treated may be displayed on the graphic display 7 either permanently, or on demand from the user, for example after pressing a dedicated key.

As illustrated in FIG. 1, the graphic display 7 may display several selectable choices 9a-9d each corresponding to a specific given action.

For example, the display 7 may display, in the form of keys or the like:
- a first given choice 9a corresponding to a start of the treatment by administering the therapeutic gas to the patient, namely a "Start treatment" key;
- a second given choice 9b corresponding to the end of the treatment of the patient concerned, namely an "End treatment" key;
- a third given choice 9c corresponding to a suspension of the treatment with temporary interruption of the administration of therapeutic gas to the patient concerned, namely a pausing of the treatment by selecting a "Pause treatment" key; and
- a fourth given choice 9d corresponding to the resumption of the treatment of the given patient by selecting a "Resume treatment" key.

The user's selection of one of these choices 9a-9d, for example by pressing with a digit on the virtual key, for example a window or the like, of the touchscreen of the display 7, will be transmitted to the microprocessor of the control means 6 and the latter will control the operation of the apparatus according to the selection made.

For example, the control means 6 may command the valve means 5 to:
- allow gas to circulate in the internal passage 2, through the flow-control electrovalve(s) according to the set flow rate (Q), in the direction of the patient if the key pressed corresponds to the first given choice 9a, namely corresponds to starting treatment by administering the therapeutic gas to the patient, namely corresponds to the "Start treatment" key;
- interrupt the circulation of gas in the internal passage 2 in the direction of the patient if the key pressed corresponds to the second or third given choice 9b or 9c, and therefore corresponds to a definitive or temporary stopping of the treatment of the patient, namely corresponds to an "End treatment" or "Pause treatment" key; and
- allow gas to circulate once again in the internal passage 2, in the direction of the patient, if the key pressed corresponds to the fourth given choice 9d, after the pressing of the key for the third given choice 9c synonymous with temporarily stopping the treatment, i.e. temporarily pausing the treatment, by selecting the "Resume treatment" key.

In the embodiment of FIG. 1, the 4 choices 9a-9d are individual keys each performing a specific action. However, some of the actions/choices could, according to other embodiments, be selected using the one same key, which means to say that the one same key could be used to select a number of different choices.

For example, the third and fourth given choices 9c and 9d are displayed in the form of two, "Pause treatment" and "Resume treatment", virtual keys or the like. However, according to another embodiment, these third and fourth given choices 9c, 9d could be selected by the one same "Pause/Resume treatment" virtual key.

Likewise, according to yet another embodiment, the first, third and fourth given choices 9a, 9c, 9d could be selected by the one same "Start/Pause/Resume treatment" virtual key.

According to yet another embodiment, the one same key could command the start and resumption of the treatment after a pause, and another key could command the temporary pausing and the definitive ending of the treatment.

Of course, other combinations or embodiments are also possible.

In all cases, a pressing, i.e. selection by the user, on the key or the like corresponding to the first given choice 9a, namely to a start of treatment in a patient concerned (i.e. new patient), causes the counter of the number of patients treated to be incremented by +1 and no further incrementation by +1 can take place until after the key corresponding to the second given choice 9b, namely the key signalling the definitive end of treatment of the patient concerned, has been pressed. It must be emphasized that a selection of given choices 9c, 9d corresponding to pausing and/or resuming a treatment does not lead to any incrementing of the counter.

According to a variant embodiment, the start of a treatment by administering therapeutic gas to a patient cannot begin until after the user has validated, i.e. confirmed, the first given choice selected by pressing the "Start treatment" key; as a preference, validation is performed by the user selecting a dedicated Validate key, particularly a virtual Validate key displayed on the graphic display 7 as detailed hereinbelow.

In other words, the control means 6 are configured to operate the valve means 5 and begin the supply of therapeutic gas only after the user has selected the first given choice of "Start treatment" and then confirmed this choice by pressing the Validate key.

Furthermore, according to a more sophisticated embodiment of the invention, the control means 6 are also configured to determine a total treatment duration for each patient treated which corresponds to the period of time elapsed between the user selecting the first given choice 9a corresponding to the start of a treatment by administering the therapeutic gas to a patient concerned, and the second given choice 9b corresponding to the definitive end of the treatment by administering therapeutic gas to the patient concerned.

As a result, the control means 6 are configured to temporarily interrupt, i.e. stop, determining the total treatment duration for a patient concerned after the user selects the third given choice 9c corresponding to pausing the treatment with temporary interruption of the administration of therapeutic gas to the patient concerned, and then resume determining the total treatment duration after:
- either the user reselects the first given choice 9a corresponding to the start of a treatment by administering the therapeutic gas,
- or the selection of a fourth given choice 9d corresponding to resumption of a treatment by administering the therapeutic gas to the patient concerned.

According to yet another embodiment of the invention, the control means 6 may also be configured to determine:
- the number of short treatments (TC) for which the total treatment duration is below a preset threshold duration, i.e. the number of patients that have undergone such a short-duration treatment, for example of under 3 h, and/or
- the number of long treatments (TL) for which the total treatment duration is above the preset threshold duration, where TL=N−TC, where N is the total number of patients treated, i.e. the number of patients that have undergone such a long-duration treatment, for example of over 3 h, and which may last for as much as 1 to several days.

The control means 6 cooperate with the graphic display 7 to display 11, 12 the value or values thus determined, namely the number of short treatments (TC) and/or the number of long treatments (TL).

Specifically, being able to determine and display the number of short treatments (TC) and the number of long treatments (TL) out of the total number of patients treated, namely the total number of treatments given using the device concerned, makes it possible to make a distinction between those patients that have been responsive to the treatment, which is to say those for whom the gas has worked, and those for whom the gas has had no therapeutic effect despite having been administered for a minimum duration, which is to say a duration that may reach the preset threshold duration. Such information is very useful to the care-giving staff, notably in order to decide whether perhaps to change the treatment.

For example, for an iNO treatment, said threshold duration may be set at 3 hours or at some other "short" duration. Treatments that are stopped before the 3-hour mark will be counted as short treatments (TC) that have had no appreciable or proven therapeutic effect in the patients, and those which have lasted at least 3 hours will be counted as long treatments (TL) that have had a beneficial effect on the patients.

In general, the counting of the patients treated with the gas administering device 1 of the invention is handled by an algorithm run by a microprocessor of the control means 6 of the device 1. This algorithm counts up the total number (N) of patients treated by incrementing a counter. This number N is displayed on the graphic display 7 in order to provide this information to the user. It is preferably recorded in a non-volatile memory.

Advantageously, the device 1 is also able to take into account the starting of a complete new treatment (i.e. new treatment for a new patient), a temporary pausing of treatment, the resumption of a treatment of an unstable patient in the withdrawal phase (i.e. resumption of a treatment that had been paused) and a "short" treatment when the duration of administration of a new treatment is less than a few hours (i.e. preset threshold duration), signifying that the patient is not responding to the treatment given.

The unique triggering event that causes the counter of the total number (N) of patients treated to be incremented by +1 is the action of selecting a first given choice 9a displayed on the touchscreen of the display 7 corresponding to "Start new treatment" by pressing a virtual key or the like displayed on the screen, corresponding to this first given choice 9a.

When it is necessary to temporarily pause the treatment of a given patient, the device 1 may offer a choice or a selection corresponding to temporarily pausing the treatment, in the form of a dedicated third given choice 9c of the "Pause treatment" type, as explained hereinabove.

When resuming a treatment, for example after a lengthy pause, the device 1 may request confirmation, i.e. validation of the choice, before incrementing the counter, for example by asking the user to select a "Yes" or "No" answer to a question of the type: "Is this a new patient?" and by offering two possible choices of answer "Yes" and "No" in the form of two virtual keys displayed on the screen. The answer "No" is treated by the device 1 as being a restart after a pause in treatment and not as a new patient; therefore the counter is not incremented.

The total treatment time is determined by the control means 6 as being the duration extending between the user pressing the first given choice 9a signifying "Start new treatment" and subsequent pressing on another key corresponding to a choice 9b of the "Stop treatment" type, or even on another key corresponding to a third given choice 9c of the "Pause treatment" type with the treatment not then being subsequently resumed with the same patient, as explained hereinabove.

Advantageously, the display 7 displays not only the total number (N) of patients treated (at 10) but also the number of short treatments TC (at 11) and the number of long treatments TL, which is to say complete treatments (at 12). The total number (N) of patients treated is equal to the sum of the total number of long treatments and the number of short treatments (i.e. N=TL+TC).

The display 10, 11, 12 of all or some of the values N, TL and TC may be available permanently on the graphic display 7 or else may appear on the screen only after being called up by the user, for example by pressing a dedicated key or the like.

FIG. 2 schematically indicates one embodiment of a gas administering installation 20 according to the invention, in this instance comprising two cylinders 21 of therapeutic gas, namely in this instance $NO/N_2$ mixtures, for example containing 800 ppm by volume of NO (the rest being $N_2$), which supply an $NO/N_2$ mixture to a therapeutic-gas supply device 1 according to the invention, as illustrated in FIG. 1 and described hereinabove.

The gas cylinders 21 are fluidically connected to the gas supply device 1 via gas conveying lines 30, such as flexible tubes or the like, which may be fitted with gas-pressure regulating and/or monitoring devices 31, such as pressure regulators, pressure gauges, etc. The gas conveying lines 30 are connected to one or more gas inlets 3 of the gas supply device 1 which supply the internal passage 2 of said gas supply device.

It will be noted that the gas supply device 1 also comprises an oxygen inlet 32 fluidically connected, via an oxygen conveying line 34, such as a flexible tube or the like, to a source of oxygen, for example the hospital network, namely an oxygen supply line running through the hospital building.

Furthermore, a medical ventilator 23, namely a respiratory assistance apparatus, is also provided to supply air or an oxygen/nitrogen ($N_2/O_2$) mixture, namely a flow of respiratory gas containing at least 21% oxygen.

The medical ventilator 23 and the gas supply device 1 are in fluidic communication with a gas supply line 22 used to carry the flow of gas to the patient.

The gas supply device 1 delivers an $NO/N_2$ mixture, for example 800 ppmv of NO, into the gas supply line 22, via an injection pipe 37, so as to inject (at 37a) a flow of $NO/N_2$ into the flow of air or of oxygen/nitrogen mixture delivered by the medical ventilator 23.

The gas supply line 22 further comprises a gas humidifier 24 arranged downstream of the flow rate sensor (at 36) at which the therapeutic-gas supply device 1 is fluidically connected to the supply line 22. This gas humidifier 24 allows the flow of gas, e.g. $NO/N_2$/air mixture, to be humidified before it is inhaled by the patient, via a patient respiratory interface, such as a tracheal tube or the like. In FIG. 2 the patient/interface assembly is indicated schematically as an "artificial lung" 25.

A line 27 for recovering the gases exhaled by the patient is also provided. The gas supply line 22 and the exhaled-gas recovery line 27 are connected to a connection piece 28, preferably a connection piece 28, and thus define a patient circuit 29. The gas supply line 22 forms the inspiratory branch of the patient circuit 29, while the exhaled-gas recovery line 27 forms the expiratory branch of the patient circuit 29.

The gas supply line 22 is fluidically connected to an outlet port 23a of the medical ventilator so as to collect and convey the gas, typically air (or an $N_2/O_2$ mixture containing around 21% $O_2$), delivered by the medical ventilator 23, while the exhaled-gas recovery line 27 is fluidically connected to an inlet port 23b of the medical ventilator 23 so as to supply the medical ventilator 23 with all or some of the flow of gases exhaled by the patient.

The exhaled-gas recovery line 27 may comprise one or more other optional components 26, such as, for example, a device for eliminating the $CO_2$, i.e. a $CO_2$ trap, such as a hot pot or the like, allowing the removal of the $CO_2$ present in the gases exhaled by the patient, or a filter or the like. Specifically, a device for eliminating the $CO_2$ may prove beneficial when the gas contains $N_2O$ that needs to be recovered after it has been exhaled by the patient. The exhaled-gas recovery line 27 is used, in the case of NO, by the ventilator 23 to check whether there is a gas leak in the line 22, 27 for example.

A flow rate sensor 36, for example of the hot-wire or differential-pressure type, is also provided, connected to the gas supply device 1 via a flow rate measurement line 35 used for measuring the flow rate of gas (Q'), such as air (i.e. $N_2/O_2$), coming from the ventilator 23, within the supply line 22 upstream of the point (at 37a) of NO/N$_2$/air connection and mixing. As explained hereinabove, this notably allows the passage of the NO through the valve means of the device 1 to be regulated.

Furthermore, a gas withdrawing line 38 fluidically connecting the gas supply device 1 to the supply line 22 in the vicinity of the Y-piece 28 may be provided so that samples of gas can be taken and their compliance with the desired mixture that is to be administered to the patient verified. The withdrawing line 38 is connected to the line 22 downstream of (at 38a) the point 37a of connection of the injection pipe 37, when considering the direction in which the flow of gas circulates from the ventilator 23 towards the patient.

FIG. 3 schematically indicates one embodiment of the screen of the graphic display 7 for a gas supply device 1 according to the invention, and which is configured to display various items of information, such as the NO, O$_2$ and NO$_2$ concentrations in the gas but also, according to the invention, a "Start treatment" touch-sensitive key (i.e. window) allowing the user, i.e. a caregiver, to select a first given choice 9a corresponding to the starting of a treatment by administering NO to a patient, and also incidentally the number "N" (at 10) of patients that have been treated with this device 1.

In this embodiment, the other choice or choices 9b-9d are not displayed until after the user has selected the first given choice 9a, i.e. until after the window that forms a touch-sensitive key on the touchscreen has been pressed.

Because the problems with recording the number of patients treated is a wide-ranging problem for public and private hospital settings alike, the device of the invention can be used for treatments other than that of inhaled nitric oxide, i.e. iNO, for example for treatments using an equimolar mixture of oxygen and nitrous oxide, such as MEOPA, or using other gases, for example argon.

The invention claimed is:

1. A device for supplying therapeutic gas, comprising:
   an internal passage through which flow of the therapeutic gas between a gas inlet and a gas outlet is to be conveyed,
   at least one valve configured to control the flow of the therapeutic gas in the internal passage,
   a controller configured to control the at least one valve,
   a graphic display configured to display choices that can be selected by a user, and
   a user interface configured to allow a selection by the user from among the choices displayed on the graphic display,
   wherein the controller is configured to count a total number (N) of patients treated by administration of the therapeutic gas from the selection, by the user, via the user interface, of a first given choice corresponding to a start of a treatment by administering the therapeutic gas to a patient concerned,
   wherein the controller is configured to determine a total duration of treatment for each patient treated which corresponds to a period of time elapsed between the user selecting:
      the first given choice corresponding to the start of treatment by administering the therapeutic gas to the patient concerned, and
      a second given choice corresponding to an end of treatment by administering the therapeutic gas to the patient concerned, and
   wherein the controller is configured to determine, from the total number (N) of patients treated, which has been counted up, and from the total durations of treatment determined for the patients treated:
      a number of short treatments (TC) for which the total duration of treatment is below a preset threshold duration, and
      a number of long treatments (TL) for which the total duration of treatment is above the preset threshold duration.

2. The device according to claim 1, wherein the controller is configured to cooperate with the graphic display to display the total number (N) of patients treated.

3. The device according to claim 1, wherein the controller comprises at least one microprocessor.

4. The device according to claim 1, wherein the user interface comprises selection keys or the graphic display comprises a touchscreen.

5. The device according to claim 4, wherein the graphic display comprises the touchscreen and the selection keys are virtual keys displayed on the touchscreen.

6. The device according to claim 1, wherein the user interface is configured to count the total number (N) of patients treated by incrementing a patients counter.

7. The device according to claim 1, wherein the controller is configured to increment the total number (N) of patients treated by +1 in response to the selection, by the user, of the first given choice corresponding to the start of treatment by administering the therapeutic gas to the patient concerned.

8. The device according to claim 1, wherein the controller is configured to:
   temporarily interrupt determining the total duration of treatment for the patient concerned after:
   either the user selects the second given choice corresponding to the end of treatment, or
   the user selects a third given choice corresponding to a suspension of treatment with temporary interruption of the administration of the therapeutic gas to the patient concerned, and
   resume determining the total duration of treatment for the patient concerned after:
   either the user reselects the first given choice corresponding to the start of treatment by administering the therapeutic gas,
   or the user selects a fourth given choice corresponding to a resumption of treatment by administering the therapeutic gas to the patient concerned.

9. The device according to claim 8, wherein the controller is configured not to increment a patients counter after the user reselects the first given choice corresponding to the start of treatment or selects the fourth given choice corresponding to the resumption of treatment for the patient concerned.

10. The device according to claim 1, wherein the controller is configured to cooperate with the graphic display to also display the number of short treatments (TC) and/or the number of long treatments (TL).

11. An installation for administering the therapeutic gas to a patient, comprising:
   at least one source of the therapeutic gas,
   the device according to claim 1, configured to be supplied with the therapeutic gas by the at least one source of the therapeutic gas, and
   a gas supply line configured to be supplied with the therapeutic gas by the device.

12. The installation according to claim 11, further comprising a medical ventilator in fluidic communication with the gas supply line.

13. The installation according to claim 11, wherein the at least one source of the therapeutic gas contains an NO/N2 or O2/N2O mixture.

14. The device according to claim 1, wherein the controller is configured to count the total number (N) of patients treated by incrementing a patients counter, and wherein the patients counter is a counter internal to a microprocessor.

15. The installation according to claim 11, wherein the at least one source of the therapeutic gas includes an NO/N2 or O2/N2O mixture stored in one or more gas containers.

16. The device according to claim 1, wherein the controller comprises at least one microcontroller.

17. The device according to claim 2, wherein the controller comprises at least one microprocessor.

18. The device according to claim 6, wherein the controller is configured to increment the total number (N) of patients treated by +1 in response to the selection, by the user, of the first given choice corresponding to the start of treatment by administering the therapeutic gas to the patient concerned.

19. A device for supplying therapeutic gas, comprising:
an internal passage through which flow of the therapeutic gas between a gas inlet and a gas outlet is to be conveyed,
at least one valve configured to control the flow of the therapeutic gas in the internal passage,
a graphic display configured to display choices that can be selected by a user,
a user interface configured to allow a selection by the user from among the choices displayed on the graphic display, and
circuitry configured to:
control the at least one valve,
count a total number (N) of patients treated by administration of the therapeutic gas from the selection, by the user, via the user interface, of a first given choice corresponding to a start of a treatment by administering the therapeutic gas to a patient concerned,
determine a total duration of treatment for each patient treated which corresponds to the period of time elapsed between the user selecting:
the first given choice corresponding to the start of the treatment by administering the therapeutic gas to the patient concerned, and
a second given choice corresponding to an end of the treatment by administering the therapeutic gas to the patient concerned, and
determine, from the total number (N) of patients treated, which has been counted up, and from the total durations of treatment determined for the patients treated:
i) a number of short treatments (TC) for which the total duration of treatment is below a preset threshold duration, and
ii) a number of long treatments (TL) for which the total duration of treatment is above the preset threshold duration.

20. The device according to claim 19, wherein the circuitry is further configured to cooperate with the graphic display to also display the number of short treatments (TC) and/or the number of long treatments (TL).

* * * * *